Figure 1:
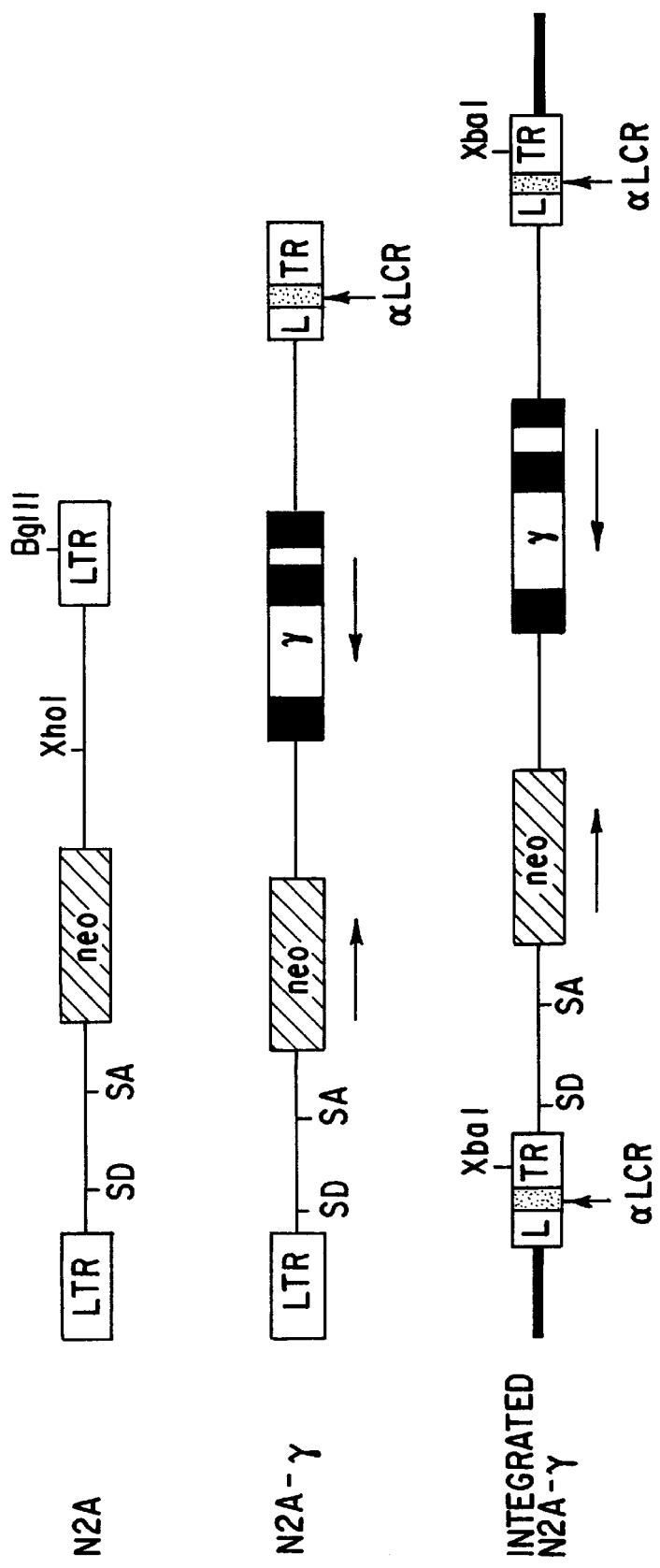

United States Patent [19]
Atweh

[11] Patent Number: 6,022,738
[45] Date of Patent: *Feb. 8, 2000

[54] VECTORS FOR EXPRESSION OF GLOBIN GENES

[75] Inventor: George F. Atweh, New York, N.Y.

[73] Assignee: Mount Sinai School of Medicine of the City University of New York, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/806,326

[22] Filed: Feb. 26, 1997

Related U.S. Application Data

[63] Continuation of application No. 08/398,160, Mar. 3, 1995, abandoned.

[51] Int. Cl.[7] .............................. C12N 15/00; C12N 5/00
[52] U.S. Cl. ...................... 435/320.1; 435/325; 435/455; 435/456
[58] Field of Search ........................... 514/44; 435/172.3, 435/320.1, 325, 355, 455, 456, 363, 372; 424/93.1, 93.21, 93.2; 536/23.1, 23.5, 24.1; 935/9, 22, 32, 33, 62, 66

[56] References Cited

FOREIGN PATENT DOCUMENTS

WO 9222646  12/1992  WIPO .
WO 9325071  12/1993  WIPO .

OTHER PUBLICATIONS

Miller, et al., Proc. Natl. Acad. Sci. U.S.A. 91:10183–10187, 1994.
Armitage, N. Engl. J. Med. 330:827–838, 1994.
Bienzle et al., Proc. Natl. Acad. Sci. U.S.A. 91:350–354, 1994.
Kasahara et al., Science 266:1373–1376, 1994.
Plavec et al., Blood 81:1384–1392, 1993.
Ren et al., Blood 81:1058–1066, 1993.
Stewart et al., Blood 81:2566–2571, 1993.
van den Bos et al., BMT 12:9–13, 1993.
Carter et al., Blood 79:356–364, 1992.
Chang et al., Proc. Natl. Acad. Sci. U.S.A. 89:3107–3110, 1992.
Pondel et al., Nucleic Acids Res. 20:237–243, 1992.
Walsh et al., Proc. Natl. Acad. Sci. U.S.A. 89:7257–7261, 1992.
Jarman et al., Mol. Cel Biol. 11:4679–4689, 1991.
Trudel et al., EMBO J. 10:3157–3165, 1991.
Carter et al., Exper. Hematol. 18:995–1001, 1990.
Fraser et al., Blood 76:1071–1076, 1990.
Higgs et al., Genes and Dev. 4:1588–1601, 1990.
Miller, Human Gene Therapy 1:5–14, 1990.
Nolta et al., Blood 75:787–797, 1990.
Novak et al., Proc. Natl. Acad. Sci. U.S.A. 87:3386–3390, 1990.
Bodine et al., Proc. Natl. Acad. Sci. U.S.A. 86:8897–8901, 1989.
Hantzopoulos et al., Proc. Natl. Acad. Sci. U.S.A. 86:3519–3523, 1989.
Bender et al., Mol. Cel. Biol. 8:1725–1735, 1988.
Dzierzak et al., Nature 331:35–41, 1988.
Markowitz, et al., Virology 167:400–406, 1988.

(List continued on next page.)

*Primary Examiner*—Deborah Crouch
*Assistant Examiner*—Deborah J. R. Clark
*Attorney, Agent, or Firm*—Baker & Botts, L.L.P.

[57] ABSTRACT

The present invention relates to vectors comprising an α-globin locus control region (αLCR) and a gene encoding an erythroid protein. In particular embodiments, a retroviral vector comprising an αLCR and a globin gene may be used to treat globin-based genetic disorders, including sickle cell anemia and β-thalassemia.

12 Claims, 8 Drawing Sheets

OTHER PUBLICATIONS

Markowitz et al., J. Virol. 62:1120–1124, 1988.
Miller et al., J. Virol. 62:4337–4345, 1988.
Armentano et al., J. Virol. 61:1647–1650, 1987.
Cone et al., Mol. Cel. Biol. 7:887–897, 1987.
Grosveld et al., Cell 51:975, 1987.
Karlsson et al., Proc. Natl. Acad. Sci. U.S.A. 84:2411–2415, 1987.
Miller, et al., Mol. Cell Biol. 6:2895–2902, 1986.
Johnson, et al., N. Eng. J. Med. 311:780–783, 1984.
Skow et al., Cell 34:1043–1052, 1983.
Thomas et al., Lancet 2:227–228, 1982.
Apperley, Bailliere's Clinical Haematology, 6(1): 299–325(1993).
Kiem et al., Current Opinion in Oncology, 7:107–114(1995).
Stamatoyannopoulos, Western J. Medicine, 157: 631–636(1992).
Rixon et al., Biochemistry, 29:4393–4400 (1990).
Walsh et al., Proc. Soc. Exp. Biol. Med., 204(3): 289–300 (1993).

```
acatgct
ttagctttaa actacaggcc tcactggagc tacagacaag aagtaaaaa acggctgaca
aaagaagtcc tggtatcctc tatgatggga gaaggaaact agctaaaagg aagaataaat
tagagaaaaa ctggaatgac tgaatcggaa caaggcaaag gctataaaaa aaattaagca
gcagtatcct cttggggcc ccttccccac actatctcaa tgcaaatatc tgtctgaaac
ggtccctggc taaactccac ccatgggttg gccagccttg ccttgaccaa tagcctttgac
aaggcaaact tgaccaatag tcttagagta tccagtgagg ccaggggccg gcggctggct
aggatgaag ataaaagga agcaccctc agcagttcca cacactcgct tctggaacgt
ctgagattat caataagctc ctagtccaga cgccatgggt catttcacag aggagacaa
ggctactatc acaagcctgt gggcaaggt gaatgtgaa gatgctggag gagaaaccct
gggaaggtag gctctggtga ccaggacaag ggagggaagg aaggacctg tgcctgcaa
aagtccaggt cgcttctcag gatttgtggc accttctgac tgtcaaactg ttcttgtcaa
tctcacagc tcctggttgt ctaccatgg accagaggt tctttgacag ctttggcaac
ctgtcctctg cctctgccat catgggcaac cccaaagtca agcacatgg caagaaggtg
ctgacttcct tgggagatgc cataaagcac ctggatgatc tcaagggcac ctttgcccag
ctgagtgaac tgcactgtga caagctgcat gtggatcctg agaacttcaa ggtgagtcca
ggagatgtt cagcactgtt gcctttagtc tcgaggcaac ttagacaact ggtattgat
ctgagcacag cagggtgtga gctgtttgaa gatactgggg ttgggagtga agaaactgca
gaggactaac tgggctgaga cccagtggca atgtttagg gcctaaggag tgcctctgaa
```

FIG. 5A

```
aatctagatg gacaactttg actttgagaa aagagaggtg gaaatgagga aaatgacttt
tcttattag  attcggtag  aaagaactt  cacctttccc ctattttgt  tattcgtttt
aaacatcta  tctggaggca ggacaagtat ggtcgttaaa aagatgcagg cagaaggcat
atattgctc  agtcaaagtg gggaactttg gtggccaaac atacattgct aaggctattc
ctatatcagc tggacacata taaaatgctg ctaatgctc  attacaaact tatatcctt
aattccagat ggggcaaag  tatgtccagg ggtgaggaac aattgaaaca tttgggctgg
agtagattt  gaaagtcagc tctgtgtgtg tgtgtgtgtg tgtgtgtc   agcgtgtgtt
tcttttaacg tcttcagcct acaacataca gggttcatgg tgggaagaag atagcaagat
ttaaattatg gccagtgact agtgcttgaa ggggaacaac tacctgcatt taatgggaag
gcaaaatctc aggctttgag ggaagttaac ataggcttga ttctgggtgg aagctgggtg
tgtagttatc tggaggccag gctggagctc tcagctcact atgggttcat ctttattgtc
tccttcatc  tcaacagctc ctgggaaatg tgctggtgac cgttttggca atccatttcg
gcaaagaatt cacccctgag gtgcaggctt cctggcagaa gatggtgact gcagtggcca
gtgccctgtc ctccagatac cactgagcct cttgcccatg attcagagct ttcaaggata
ggcttattc  tgcaagcaat acaaataata aatctattct gctgagagat cacacatgat
tttcttcagc tctttttttt acatctttt  aaatatatga gccacaaagg gtttatattg
agggagtgt  gtatgtgtat ttctgcatgc ctgtttgtgt ttgtggtgtg tgcatgctcc
tcatttattt ttatatgaga tgtgcatttt gatgagcaaa taaaagcagt aaagacactt
gt
```

FIG. 5B

```
    tct ggaacctatc agggaccaca gtcagccagg caagcacatc tgcccaagcc
aagggtggag gcatgcagct gtggggtct gtgaaaacac ttgagggagc agataactgg
gccaaccatg actcagtgct tctggaggcc aacaggactg ctgagtcatc ctgtgggggt
ggaggtggga caagggaaag gggtgaatgg tactgctgat tacaacctct ggtgctgcct
ccccctcctg tttatctgag ag
```

FIG.6

```
  1 tcgaccctct ggaacctatc agggaccaca gtcagccagg caagcacatc tgcccaagcc
 61 aagggtggag gcatgcagct actcagtgct gtggggtct gtgaaaacac ttgagggagc agataactgg
121 gccaaccatg actcagtgct tctggaggcc aacaggactg ctggtcatc ctgtgggggt
181 ggaggtggga caagggaaag gggtgaatgg tactgctgat tacaacctct ggtgctgcct
241 cccctcctg tttatctgag agggaaggcc atgcccaaag tgttcacagc caggcttcag
301 gggcaaagcc tgacccagac agtaaatacg ttcttcatct ggagctgaag aaattc
```

FIG.7

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..19

(xi) SEQUENCE DESCRIPTION: SEQ ID NO:1:

TCTGGAACCT ATCAGGGAC                                               19

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:

-continued

```
        (A) NAME/KEY: misc_feature
        (B) LOCATION: 1..22

(xi) SEQUENCE DESCRIPTION: SEQ ID NO:2:

CTCTCAGATA AACAGGAGGG GG                                                22

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..22

(xi) SEQUENCE DESCRIPTION: SEQ ID NO:3:

TTTCTGGATT CATCGACTGT GG                                                22

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..21

(xi) SEQUENCE DESCRIPTION: SEQ ID NO:4:

AAAGTCCTTG GGGTCTTCTA C                                                 21

(2) INFORMATION FOR SEQ ID NO:5:

(i) SEQUENCE CHARACTERISTICS:
        (A) LENGTH: 2169 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..2169

(xi) SEQUENCE DESCRIPTION: SEQ ID NO:5:

ACATGCTTTA GCTTTAAACT ACAGGCCTCA CTGGAGCTAC AGACAAGAAG GTAAAAACG         60

GCTGACAAAA GAAGTCCTGG TATCCTCTAT GATGGGAGAA GGAAACTAGC TAAAGGGAAG       120

AATAAATTAG AGAAAAACTG GAATGACTGA ATCGGAACAA GGCAAAGGCT ATAAAAAAAA       180

TTAAGCAGCA GTATCCTCTT GGGGGCCCCT TCCCCACACT ATCTCAATGC AAATATCTGT       240

CTGAAACGGT CCCTGGCTAA ACTCCACCCA TGGGTTGGCC AGCCTTGCCT TGACCAATAG       300

CCTTGACAAG GCAAACTTGA CCAATAGTCT TAGAGTATCC AGTGAGGCCA GGGGCCGGCG       360

GCTGGCTAGG GATGAAGAAT AAAAGGAAGC ACCCTTCAGC AGTTCCACAC ACTCGCTTCT       420

GGAACGTCTG AGATTATCAA TAAGCTCCTA GTCCAGACGC CATGGGTCAT TTCACAGAGG       480

AGGACAAGGC TACTATCACA AGCCTGTGGG GCAAGGTGAA TGTGGAAGAT GCTGGAGGAG       540
```

```
AAACCCTGGG AAGGTAGGCT CTGGTGACCA GGACAAGGGA GGGAAGGAAG GACCCTGTGC      600

CTGGCAAAAG TCCAGGTCGC TTCTCAGGAT TTGTGGCACC TTCTGACTGT CAAACTGTTC      660

TTGTCAATCT CACAGGCTCC TGGTTGTCTA CCCATGGACC CAGAGGTTCT TTGACAGCTT      720

TGGCAACCTG TCCTCTGCCT CTGCCATCAT GGGCAACCCC AAAGTCAAGG CACATGGCAA      780

GAAGGTGCTG ACTTCCTTGG GAGATGCCAT AAAGCACCTG GATGATCTCA AGGGCACCTT      840

TGCCCAGCTG AGTGAACTGC ACTGTGACAA GCTGCATGTG GATCCTGAGA ACTTCAAGGT      900

GAGTCCAGGA GATGTTTCAG CACTGTTGCC TTTAGTCTCG AGGCAACTTA GACAACTGAG      960

TATTGATCTG AGCACAGCAG GGTGTGAGCT GTTTGAAGAT ACTGGGGTTG GGAGTGAAGA     1020

AACTGCAGAG GACTAACTGG GCTGAGACCC AGTGGCAATG TTTTAGGGCC TAAGGAGTGC     1080

CTCTGAAAAT CTAGATGGAC AACTTTGACT TTGAGAAAAG AGAGGTGGAA ATGAGGAAAA     1140

TGACTTTTCT TTATTAGATT TCGGTAGAAA GAACTTTCAC CTTTCCCCTA TTTTTGTTAT     1200

TCGTTTTAAA ACATCTATCT GGAGGCAGGA CAAGTATGGT CGTTAAAAAG ATGCAGGCAG     1260

AAGGCATATA TTGGCTCAGT CAAAGTGGGG AACTTTGGTG GCCAAACATA CATTGCTAAG     1320

GCTATTCCTA TATCAGCTGG ACACATATAA AATGCTGCTA ATGCTTCATT ACAAACTTAT     1380

ATCCTTTAAT TCCAGATGGG GGCAAAGTAT GTCCAGGGGT GAGGAACAAT TGAAACATTT     1440

GGGCTGGAGT AGATTTTGAA AGTCAGCTCT GTGTGTGTGT GTGTGTGTGT GTGTGTCAGC     1500

GTGTGTTTCT TTTAACGTCT TCAGCCTACA ACATACAGGG TTCATGGTGG GAAGAAGATA     1560

GCAAGATTTA AATTATGGCC AGTGACTAGT GCTTGAAGGG GAACAACTAC CTGCATTTAA     1620

TGGGAAGGCA AAATCTCAGG CTTTGAGGGA AGTTAACATA GGCTTGATTC TGGGTGGAAG     1680

CTGGGTGTGT AGTTATCTGG AGGCCAGGCT GGAGCTCTCA GCTCACTATG GGTTCATCTT     1740

TATTGTCTCC TTTCATCTCA ACAGCTCCTG GGAAATGTGC TGGTGACCGT TTTGGCAATC     1800

CATTTCGGCA AGAATTCAC CCCTGAGGTG CAGGCTTCCT GGCAGAAGAT GGTGACTGCA     1860

GTGGCCAGTG CCCTGTCCTC CAGATACCAC TGAGCCTCTT GCCCATGATT CAGAGCTTTC     1920

AAGGATAGGC TTTATTCTGC AAGCAATACA AATAATAAAT CTATTCTGCT GAGAGATCAC     1980

ACATGATTTT CTTCAGCTCT TTTTTTTACA TCTTTTTAAA TATATGAGCC ACAAAGGGTT     2040

TATATTGAGG GAAGTGTGTA TGTGTATTTC TGCATGCCTG TTTGTGTTTG TGGTGTGTGC     2100

ATGCTCCTCA TTTATTTTTA TATGAGATGT GCATTTTGAT GAGCAAATAA AAGCAGTAAA     2160

GACACTTGT                                                             2169

(2) INFORMATION FOR SEQ ID NO:6:

(i) SEQUENCE CHARACTERISTICS:
        (A) LENGTH: 255 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..255

(xi) SEQUENCE DESCRIPTION: SEQ ID NO:6:

TCTGGAACCT ATCAGGGACC ACAGTCAGCC AGGCAAGCAC ATCTGCCCAA GCCAAGGGTG       60

GAGGCATGCA GCTGTGGGGG TCTGTGAAAA CACTTGAGGG AGCAGATAAC TGGGCCAACC      120

ATGACTCAGT GCTTCTGGAG GCCAACAGGA CTGCTGAGTC ATCCTGTGGG GGTGGAGGTG      180
```

-continued

```
GGACAAGGGA AAGGGGTGAA TGGTACTGCT GATTACAACC TCTGGTGCTG CCTCCCCCTC      240

CTGTTTATCT GAGAG                                                       255

(2) INFORMATION FOR SEQ ID NO:7:

(i) SEQUENCE CHARACTERISTICS:
        (A) LENGTH: 356 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..356

(xi) SEQUENCE DESCRIPTION: SEQ ID NO:7:

TCGACCCTCT GGAACCTATC AGGGACCACA GTCAGCCAGG CAAGCACATC TGCCCAAGCC       60

AAGGGTGGAG GCATGCAGCT GTGGGGGTCT GTGAAAACAC TTGAGGGAGC AGATAACTGG      120

GCCAACCATG ACTCAGTGCT TCTGGAGGCC AACAGGACTG CTGAGTCATC CTGTGGGGGT      180

GGAGGTGGGA CAAGGGAAAG GGGTGAATGG TACTGCTGAT TACAACCTCT GGTGCTGCCT      240

CCCCCTCCTG TTTATCTGAG AGGGAAGGCC ATGCCCAAAG TGTTCACAGC CAGGCTTCAG      300

GGGCAAAGCC TGACCCAGAC AGTAAATACG TTCTTCATCT GGAGCTGAAG AAATTC         356
```

VECTORS FOR EXPRESSION OF GLOBIN GENES

This application is a continuation of application Ser. No. 08/398,160, filed on Mar. 3, 1995, now abandoned.

The invention was made with government support under grant number HL 42919 awarded by the National Institutes of Health. The government has certain rights in the invention.

1. INTRODUCTION

The present invention relates to vectors comprising an α-globin locus control region (αLCR) and a gene encoding an erythroid protein. In particular embodiments, a retroviral vector comprising an αLCR and a globin gene may be used to treat globin-based genetic disorders, including sickle cell anemia and β-thalassemia.

2. BACKGROUND OF THE INVENTION

A variety of blood diseases are caused by mutations involving the structure or expression of erythroid proteins. Mutations involving non-globin erythroid genes are associated with a multitude of disorders, including porphyria, sideroblastic anemia, and glucose-6-phosphate dehydrogenase deficiency. Genetic aberrations in globin gene expression result in several common blood diseases, including sickle cell anemia and β-thalassemia.

Sickle cell anemia is an autosomal recessive disorder involving a mutation in the β-globin gene that causes hemoglobin to form long polymers under deoxygenated conditions. As a result, the red blood cell is deformed and assumes a "sickle" shape which may compromise the microcirculation. Patients with this disorder have chronic anemia and typically suffer painful "sickle cell crises" and multiple end-organ damage from obstruction of blood vessels with sickled red blood cells. Medical therapy for sickle cell anemia has been largely directed toward managing the complications of vascular insufficiency caused by red cell deformation, although allogeneic bone marrow transplantation, which supplies normal red blood cells, has been shown to be effective (Johnson, et al., N. Eng. J. Med. 311:780–783, 1984).

Thalassemias are disorders associated with a diminished rate of globin synthesis, which may be a consequence of a deletion of the globin gene itself, or, more commonly, are due to mutations in regulatory sequence information. β-thalassemia is one of the most frequent single gene disorders in humans; 50,000 children are born yearly with this disease. It is marked by anemia, failure to thrive, and splenomegaly. Iron deposition caused by increased absorption and multiple transfusions often results in multiple organ system failure. As with sickle cell anemia, allogeneic bone marrow transplantation has been shown to be curative of thalassemia (Thomas et al., Lancet 2:227–228, 1982).

However, the use of allogeneic bone marrow transplant to treat either sickle cell anemia or β-thalassemia is problematic. First, the availability of a suitable donor is frequently limited. Further, in order to avoid the complication of graft vs. host disease, immunosuppressive drugs are typically administered, which are themselves associated with increased risk of infection, cancer, and a substantial mortality rate.

A potential alternative to replacement of defective red blood cells in these conditions is correction of the underlying genetic defect by introducing a normal copy of the erythroid gene that is missing or defective into the erythroid cells of the patient. The ability to design safe and efficient delivery systems for gene replacement therapy is key to improving the prospects for therapeutic intervention.

Gene delivery has been accomplished using viruses engineered to carry foreign genetic material into a cell of interest. Such viruses have included DNA viruses such as vaccinia, adenovirus, and adeno-associated virus (AAV) and RNA viruses such as retroviruses.

Retroviruses, which naturally infect and integrate their genome into a recipient host cell, are ideal vehicles for gene transfer. In order to maximize safety, the recombinant viral genome may be introduced and encapsulated in a packaging cell line to generate a replication-incompetent retroviral stock. Such virus is able to infect a target cell and introduce the gene of interest, but cannot replicate. This feature limits the function of the viral vector to being a gene transfer vehicle, and precludes the generation of potentially dangerous infectious retroviruses.

Viruses have been used to transfer genes into erythroid cells. For example, recombinant AAV vector was shown to transduce a human γ-globin gene into human erythroid K562 cells (Walsh et al., Proc. Natl. Acad. Sci. 89:7257–7261, 1992). Moreover, initial experiments, engineering retroviruses to carry globin genes using the cis-acting regulatory elements linked to the β-globin gene, resulted in low β-globin expression in erythroid cells and hematopoietic stem cells (Cone et al., Mol. Cel. Biol. 7:887–897, 1987; Karlsson et al., Proc. Natl. Acad. Sci. 84:2411–2415, 1987; Miller et al., J. Virol. 62:4337–4345, 1988; Dzierzak et al., Nature 331:35–41, 1988).

Subsequently, a major regulatory region far upstream of the β-globin gene, the β-locus control region (β-LCR) was identified (Grosveld et al., Cell 51:975, 1987). Retroviruses containing the β-globin gene under β-LCR control were found to express higher levels of β-globin (Novak et al., Proc. Natl. Acad. Sci. 87:3386–3390, 1990; Chang et al., Proc. Natl. Acad. Sci. 89:3107–3110, 1992; Plavec et al., Blood 81:1384–1392, 1993). Unfortunately, while expression of the β-globin gene was initially improved, the β-LCR element was highly recombinogenic, and frequent rearrangement of the viral sequences occurred before or after integration into host cells. This instability resulted in the production of low-titer retroviral stocks that infected hematopoietic stem cells with low efficiency.

A major upstream regulatory region of the α-globin gene cluster, the α-locus control region (α-LCR), was identified more recently and shown to function in an enhancer-like manner to increase gene expression (Higgs et al., Genes and Dev. 4:1588–1601, 1990; Ren et al., Blood 81: 1058–1066, 1993). The region is located 40 kb upstream of the gene cluster and its function is erythroid-specific. αLCR was localized to a 255 bp element (SEQ ID NO.6) and shown to confer inducible expression on a heterologous promoter (Jarman et al., Mol. Cell Biol. 11:4679–4689, 1991; Pondel et al., Nucleic Acids Res. 20:237–243, 1992; Ren et al., Blood 81:1058–1066, 1993).

3. SUMMARY OF THE INVENTION

The present invention is directed to vectors comprising an α-globin locus control region (αLCR) and a gene encoding an erythroid protein. It is based, at least in part, on the discovery that vectors comprising αLCR exhibit substantially greater stability, and consequently provide superior means for achieving erythroid-specific expression of a gene of interest, relative to hitherto known vectors. Furthermore, retroviral vectors comprising the αLCR element may be produced at high titers and are capable of infecting primary hemopoietic stem cells.

In one specific nonlimiting embodiment, the vector of the invention is a retroviral vector comprising the αLCR and the human γ-globin gene, and may be used for the treatment of genetic diseases involving β-globin, such as sickle cell anemia and β-thalassemia. In other nonlimiting embodiments, retroviral vectors may be used to construct animal models for human globin diseases.

4. BRIEF DESCRIPTION OF THE FIGURES

FIG. 1. Schematic illustration of retroviral constructs. Thin lines represent plasmid sequences and thick lines represent chromosomal sequences. The arrows indicate the direction of transcription. The relevant restriction sites are marked. SD is splice donor and SA is splice acceptor.

Figure 2:
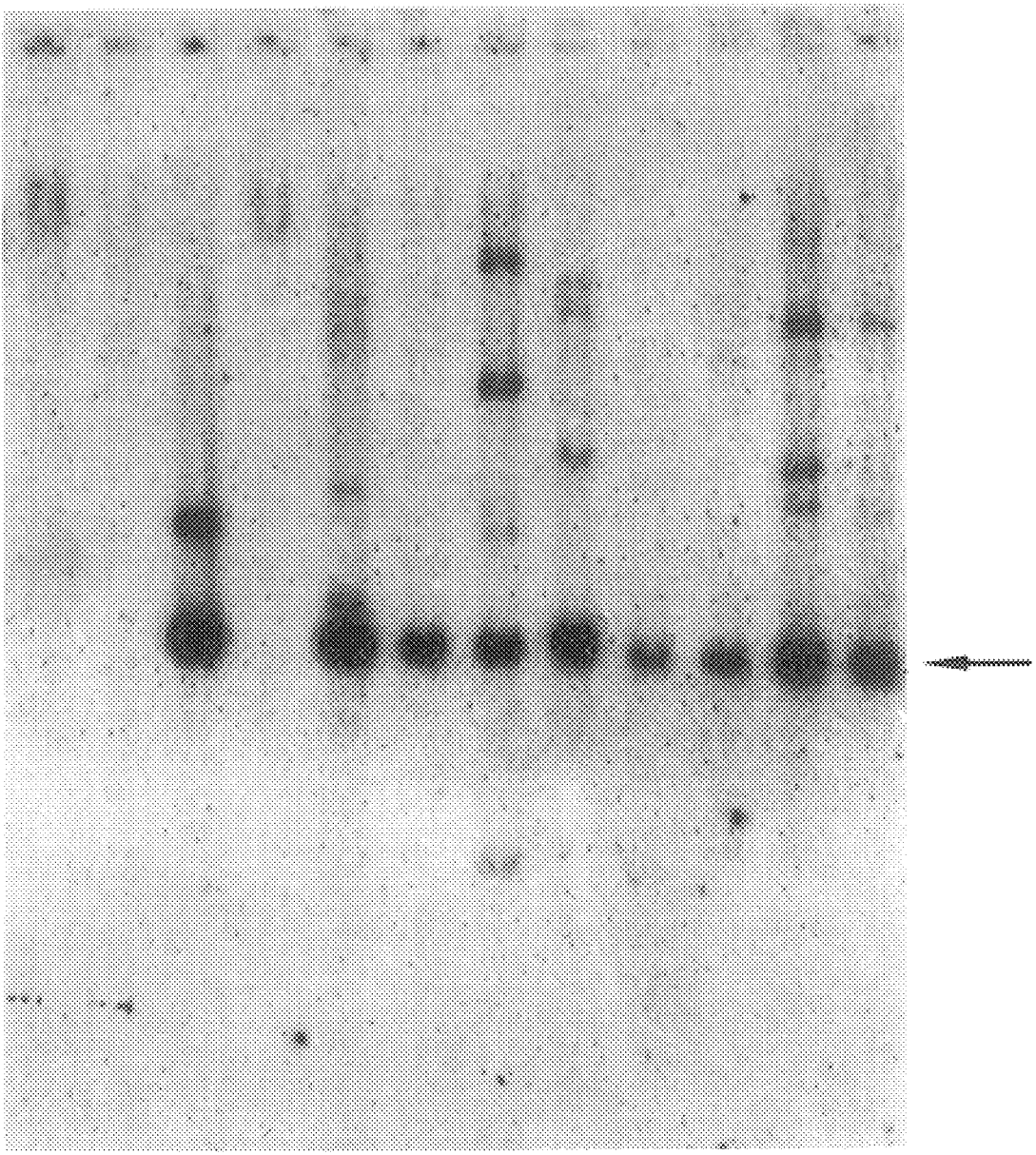

FIG. 2. Stability of integration of retroviral sequences in transfected cells. Autoradiograph of a Southern blot in which DNA from transfected GP+envAM12 cells was digested with SalI and probed with an αLCR fragment. The arrow marks the location of the expected 4.3 kb fragment.

Figure 3:
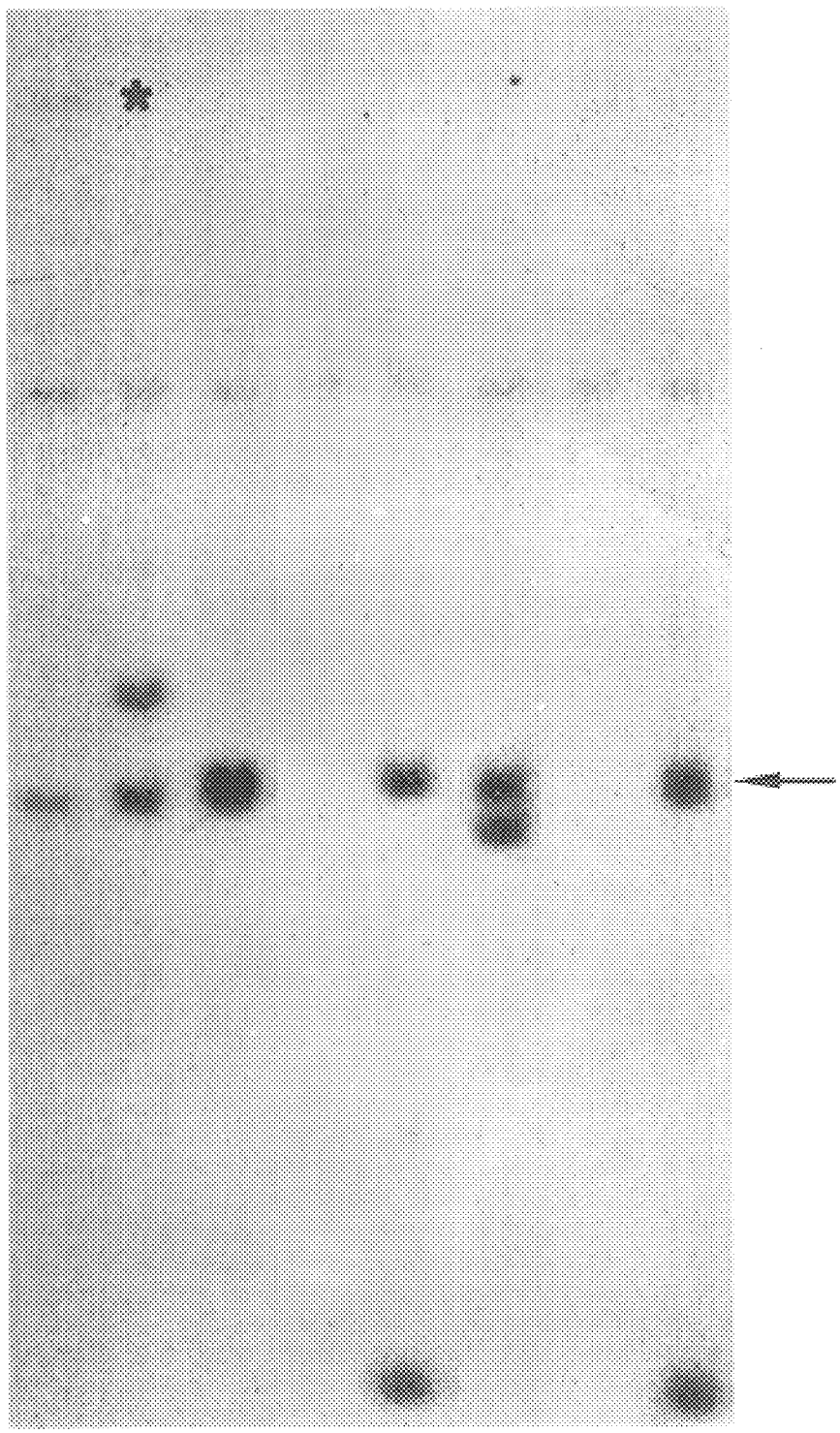

FIG. 3. Stability of integration of retroviral sequences in infected cells. Autoradiograph of a Southern blot in which DNA from infected NIH 3T3 cells was digested with XbaI and probed with an αLCR fragment. The asterisk marks the location of the constant 3 kb fragment. The other variable sized fragments result from junctional sequences at the sites of chromosomal integration. The arrow highlights a large faint band that is difficult to visualize.

FIG. 4(A–B). Expression of the transduced γ-globin genes in MEL cells. The two autoradiographs represent S1 assays for quantifying mouse $B^{maj}$ and human γ-globin mRNA in infected MEL cells. U represents RNA from uninduced cells and I represents RNA from DMSO-induced cells. (A) RNA isolated from a pool of infected MEL cells in the induced and uninduced states. (B) RNA isolated from 5 individual clones of infected MEL cells in the induced and uninduced states.

FIG. 5. The nucleic acid sequence of the normal human fetal $^A$γ-globin gene (SEQ ID NO:5).

FIG. 6. The nucleic acid sequence of the human αLCR that was cloned into N2A-γ(SEQ ID NO.6).

FIG. 7. The nucleic acid sequence of a 356 bp sequence containing the human αLCR (SEQ ID NO.7).

5. DETAILED DESCRIPTION OF THE INVENTION

The present invention provides for vectors and methods relating to the transfer and expression of genes into erythroid cells. For purposes of clarity of description, and not by way of limitation, the detailed description of the invention is divided into the following subsections:

(i) vectors of the invention;

(ii) generation of producer cell lines for retroviral vectors;

(iii) transduction of erythroid cells;

(iv) transduction of bone marrow cells;

(v) transplantation of transduced bone marrow cells;

(vi) gene therapy in animal models of human globin diseases; and (viii) utilities of the invention.

5.1. Vectors of the Invention

The present invention provides for vectors comprising an α-globin locus control region (αLCR) and a gene encoding an erythroid protein.

Suitable vectors include viral and plasmid vectors known in the art. For example, and not by way of limitation, viral vectors which may be used according to the invention are preferably retroviral or parvoviral (including adeno-associated virus) vectors. Further vectors which may be used, albeit somewhat less preferable for introduction into hematopoietic cells, include those derived from DNA viruses such as vaccinia, herpes, hepatitis, adenovirus and papilloma virus as well as those derived from RNA viruses, such as influenza viruses. In preferred, non-limiting embodiments of the invention, a retroviral vector may be used. Such vectors do not, preferably, contain retroviral genes necessary for replication. Nonlimiting examples of such replication-defective vectors include the N2 and N2A series containing sequences derived from Moloney murine leukemia virus (Armentano et al., J. Virol. 61:1647–1650, 1987; Hantzopoulos et al., Proc. Natl. Acad. Sci. U.S.A. 86:3519–3523, 1989), as well as retroviral vectors such as LNL-XHC (Bender et al., Mol. Cel. Biol. 8:1725–1735, 1988), pSVX (Cone et al., Mol. Cell. Biol. 7:887–897, 1987), and EPO or CD34-targeted viruses (Kasahara et al., Science 266:1373–1376, 1994).

The αLCR may preferably be the human αLCR in the 255 base-pair fragment (SEQ ID NO:6) located upstream from the α-globin gene (Ren, S. et al., Blood 81:1058–1066, 1993) having a sequence as set forth in FIG. 6.

An erythroid gene, as defined herein, is a gene which is expressed in a mammalian erythroid cell at any stage in the development of such cell. However, expression of the gene need not be restricted to erythroid cells for a gene to be considered an erythroid gene. Human as well as non-human erythroid genes are within the scope of the present invention. The term "gene", as used herein, refers to genomic sequences as well as their transcripts, and would therefore include, within its scope, not only the coding portion of the transcription unit, but also, for example, a cDNA ultimately generated using an mRNA transcript.

Erythroid genes which may be comprised in vectors of the invention include globin as well as non-globin erythroid genes. Globin genes which may be utilized include, but are not limited to, human globin genes, including genes present in the β-globin gene cluster, such as β-globin, epsilon-globin, $^A$γ-globin, and $^G$γ-globin genes; mutations of the genes of the human β-globin gene cluster; genes present in the human α-globin gene cluster, such as zeta-globin or α-globin genes; mutations of genes of the human α-globin gene cluster; genes encoding globin variants with a desirable property, such as favorable oxygen affinity or resistance to polymerization of the hemoglobin molecule; and non-human globin genes from, for example, pig, cow, goat, mouse or rabbit. In one specific preferred nonlimiting embodiment of the invention, the globin gene is the human fetal γ-globin gene. In other specific nonlimiting embodiments, where it is desirable to produce an animal model of a human globin disease, globin genes associated with genetic diseases, such as the sickle cell globin gene, may be incorporated into a vector of the invention.

Non-globin genes which may be comprised in vectors of the invention include, but are not limited to, genes encoding delta amino levulonic acid synthase, ferrochelatase, uroporphriniogen III cosynthetase, glucose-6 phosphate-dehydrogenase, spectrin, and protein 4.1.

Vectors of the invention may further comprise a promoter element which may be the promoter native to the erythroid gene or alternatively may be of a heterologous nature.

Vectors of the invention may be constructed so as to place the erythroid gene in proximity to the αLCR; the αLCR may be located either upstream or downstream of the erythroid gene. The αLCR and erythroid gene sequences may be assembled into the vector using conventional gene splicing techniques, (*Molecular Biology: A Laboratory Manual*, J. Sambrook et al., eds., Cold Spring Harbor Laboratory Press, 1989), or by techniques that utilize the particular features of the vector. For example, upon integration of a retroviral vector genome into a host cell, the 3' retroviral LTR is generally duplicated and transferred to the 5' LTR. Accordingly, in one nonlimiting embodiment of the invention, where the vector is a retroviral vector, the αLCR element may be cloned into the 3' LTR which may cause it to be duplicated and transferred to the 5' LTR upon integration. As a result, the inserted αLCR may be positioned upstream of the target gene which has been cloned between the LTR sequences, preferably using a polylinker which has been placed into the retroviral vector plasmid for ease of cloning.

Vectors of the invention may also comprise a selectable marker for identification of cells into which the vector has been introduced, by selecting for cell growth in the presence of an appropriate selection agent. Such selectable markers include the genes for neomycin resistance, dihydrofolate reductase (DHFR), or multidrug resistance, as well as others known to those skilled in the art.

In one specific non-limiting embodiment, a retroviral vector may be constructed as follows: the human γ-globin gene may be cloned into the unique Xho I site in the N2A vector between the neo$^r$ and 3' LTR in a reverse orientation relative to the 5' LTR as a 2.2 kb RsaI fragment (410 to +1761 of the gene sequence (SEQ ID NO.5)).

In another specific, nonlimiting embodiment, an αLCR fragment may be generated by the polymerase chain reaction by amplifying 0.5 µg of human DNA using primers designed from the 356 bp fragment (SEQ ID NO.7) (the sequence of which is set forth in FIG. 7) shown by Jarman et al., Mol. Cell. Biol. 11:4679–4689, 1991 to account for the major activity of the αLCR. Amplification parameters may include 30 cycles of synthesis, each consisting of denaturation for 1 minute at 94° C., annealing for 2 minutes at 45° C., and extension for 3 minutes at 72° C. The resulting 255 bp product (SEQ ID NO:6), having a sequence as set forth in FIG. 6, may be eluted from a preparative agarose gel, blunt-ended by DNA polymerase, and cloned into the SmaI cloning site of pBluescript II KS (Strategene, La Jolla, Calif.) for plasmid preparation by standard techniques to generate a fragment stock.

The αLCR may be cloned into the BglII site of the polylinker in the 3' LTR of N2A by blunt-end ligation.

An example of the construction of such a vector is presented in Example 6, infra, wherein the N2A-γ vector, depicted in FIG. 1, was produced. The N2A-γ retroviral vector has been deposited with the ATCC and assigned accession number 97077.

5.2. Generation of Producer Cell Lines for Retroviral Vectors

In order to produce recombinant retrovirus, a replication-defective retroviral vector, as described in section 5.1., supra, may be transfected into a packaging cell line. Such a cell line is engineered to contain retroviral genes that express the viral proteins not contained in the vector in order that the recombinant viral genome is packaged and infectious retrovirus is produced. A cell line producing an infectious form of a vector of the invention is referred to herein as a producer cell line.

The choice of a packaging cell line will determine the host range of infection for any retrovirus produced from it because the specific env gene that is engineered into the cell line will produce an env protein with a specific infectious capability (Miller, Human Gene therapy 1:5–14, 1990). For use in human cell transduction, a packaging cell line that carries an env gene capable of mediating infection of human cells may be used; for example, an amphotropic (infects cells of different species, such as murine and human cells) packaging cell line may be used. Such cell lines include GP+envAM12 (Markowitz, et al., Virology 167:400–406, 1988) and PA 317 (Miller, et al., Mol. Cell Biol.6:2895–2902, 1986). Murine cell transduction may be performed with an ecotropic (infects cells of the same species, e.g., murine cells) cell line such as GP+E-86 (Markowitz et al., J. Virol. 62:1120–1124, 1988). In a preferred embodiment of the invention, the amphotropic PA317 may be used as the packaging cell line. The newly produced retroviruses, however, would not be expected to contain the viral genes supplied by the packaging cell line (absent a rare recombination event or events), and should therefore be replication-incompetent when used for transduction, a feature that optimizes therapeutic safety.

A retroviral vector may be transfected into a packaging cell by standard techniques including calcium-phosphate precipitation, DEAE-dextran, electroporation, and others known to those skilled in the art (*Molecular Biology: A Laboratory Manual*, J. Sambrook et al., eds., Cold Spring Harbor Laboratory Press, 1989). If the vector contains a selectable marker, a selection agent may be added to the medium to select for the growth of those cells containing the vector.

Colonies of cells that grow in the presence of a selection agent may be expanded to form producer cell lines capable of generating high-titer retroviral stocks. Retrovirus quantitation may be performed by precipitating the viruses from the supernatant, isolating RNA and slot-blotting with reference to a control virus stock to determine the titer. Alternatively, serial dilutions of the retroviral vector stock may be used to infect a suitable cell line (e.g., NIH 3T3, K562), and the titer (colony-forming units cfu/ml) may be established by determining the number of colonies that grow in the presence of a selection agent (for example G418) to select for neo$^r$ cells. A producer cell line that generates a virus stock with a titer of greater than $10^6$ cfu/ml is preferred for the practice of the invention.

Non-producer cell lines may be used to assess the stability of retroviral integration. Such cell lines include, for example, murine NIH 3T3, or human K562, HeLa, HepA, which may be infected with retroviral stock and evaluated as follows.

The stability of retroviral integration into transfected or infected cells may be determined by isolating genomic DNA cut with a restriction enzyme chosen because a readily identifiable fragment may be detected if the retroviral DNA is integrated without rearrangement or deletion. The DNA may be analyzed by Southern blotting, using a probe specific for the retroviral fragment. The presence of the specific retroviral band of the appropriate size may be used to confirm that the original retroviral fragment is integrated. Alternatively, integration of the viral DNA into the genome may be detected by PCR amplification using primers containing a viral sequence, followed by Southern blotting with an appropriate probe (*Molecular Biology: A Laboratory Manual*, J. Sambrook et al., eds., Cold Spring Harbor Laboratory Press, 1989).

Because recombination between a replication-defective retroviral vector with DNA present in the producer cell line may give rise to replication-competent retrovirus, it is desirable to detect any replication-competent retrovirus produced from a producer cell line in order to ensure the safety of a retroviral vector stock for use in gene therapy. Accordingly, non-producer cells may be infected with the supernatant from a producer cell line and grown in the presence of a selection agent. The supernatant from these cells (termed "secondary supernatant") may then be used to infect fresh cells. The absence of retrovirus production consequent to exposure to the secondary supernatant is evidence that no replication-competent retrovirus was generated from the producer cell line.

Alternatively, non-producer cells may be infected with supernatant from a producer cell line with supernatant from a producer cell line and grown in the absence of a selection agent. This allows the amplification of any wild-type retroviruses. The secondary supernatant from this infection may then be applied to fresh cells to determine if any of the cells are converted to growth in the presence of the selection agent. The absence of cell growth in this experiment is evidence that no replication-competent retrovirus was generated from the producer cell line.

In another embodiment, a retroviral stock may be cycled between amphotropic and ecotropic cell lines in order to amplify any latent helper virus, which may be detected in a similar selection protocol to those set forth above (Markowitz et al., J. Virol. 62:1120–1124, 1988; Markowitz et al., Virology 167: 400–406, 1988).

5.3. Transduction of Erythroid Cells

The vectors of the invention may be introduced into erythroid cells by transduction, using standard techniques associated with the particular vector used. Alternatively, the αLCR-globin gene construct (in the presence or absence of vector-derived sequences) may be introduced by other gene transfer methods, including but not limited to, electroporation, microinjection, calcium-phosphate precipitation, plasmid-mediated entry, and others known to those skilled in the art. In some circumstances, it may be desirable to use such techniques to introduce an αLCR-erythroid gene construct into a non-erythroid cell, such as an oocyte.

Erythroid cells that may be transduced include primary erythroid cells, such as those derived from hematopoietic stem cells of bone marrow, as well as erythroid cell lines. For therapeutic purposes or for the creation of an animal model, it may be desirable to transfect bone marrow cells, as described in the following section. It may also be desirable to transduce an erythroid cell line with a vector of the invention in order to evaluate the stability of the vector and/or its ability to express globin. Suitable erythroid cell lines include human K562 cells, murine erythroleukemia (MEL) cells, and others known to those skilled in the art. In nonlimiting embodiments of the invention, the multiplicity of infection is desirably between $5\times10^3$ and $25\times10^3$ virus particles per erythroid cell.

Erythroid cell lines consist of immature cells of the erythroid lineage that have the capacity to replicate indefinitely in culture. However, in order to confirm that a vector according to the invention is associated with erythroid-specific expression of its comprised erythroid gene, cells of a transduced erythroid cell line may be induced to differentiate by exposure to an appropriate agent, e.g., hemin induction of K562 cells or dimethyl sulfoxide (DMSO) treatment of MEL cells. This exposure may activate the αLCR of the vector to increase expression of the comprised erythroid gene. Experiments performed in the presence and absence of inducing agent may be used to quantitate the inducible effect.

Analysis of the level of expression may be performed by quantitative S1 analysis or RNAse protection analysis of RNA isolated from infected cells, for example, or other methods known to those skilled in the art (*Molecular Biology: A Laboratory Manual,* J. Sambrook et al., eds., Cold Spring Harbor Laboratory Press, 1989).

Alternatively, the erythroid protein level may be assessed with protein detection techniques, including Western blotting and immunohistochemistry, for example, to determine the efficiency of transduction of the erythroid gene.

In a specific, non-limiting embodiment, retroviral vectors of the present invention may be used to infect erythroid cell lines in order to express a globin gene from the αLCR. For example, erythroid cells may be co-cultivated with a retroviral producer cell line to initiate infection or may be exposed to a supernatants from a producer cell culture.

5.4. Transduction of Bone Marrow Cells

Erythroid genes under the control of the αLCR may be transduced into bone marrow erythroid progenitor cells, as set forth in the preceding section. In specific nonlimiting embodiments of the present invention, retroviral vectors comprising globin genes under the transcriptional control of the αLCR may be transduced into bone marrow erythroid progenitor cells.

For example, and not by way of limitation, bone marrow cells may be isolated from mice for experiments to determine the efficiency of transduction, to assess the ability to transplant such transduced cells, and to produce animal models of human erythroid diseases (see infra). Mice may be administered 5-fluorouracil to increase the proportion of hemopoietic progenitors (Stewart et al., Blood 81:2566–2571, 1993). Cells may be harvested from the femurs of adult mice, and then may be washed and resuspended in tissue culture medium under standard conditions known to those skilled in the art. Growth factors may be added to the medium to induce the entry of stem cells into the cycle and improve the efficiency of their transduction (Bodine et al., Proc. Natl. Acad. Sci. 86:8897–8901, 1989). After a suitable period to allow cells to enter the cell cycle, the cells may be centrifuged and resuspended in medium containing polybrene, and then exposed to a vector according to the invention under conditions suitable for infection to occur; for example, infection with a viral stock (multiplicity of infection (MOI):5–25) may be performed by co-cultivation of these cells with a producer cell line or with supernatant derived from a producer cell line. Non-adherent cells may be recovered for transplantation into recipient mice. Mouse lines which may serve as a source for bone marrow cells include BALB/C and C57BL/6J.

One example of a large animal model for assessing the transduction of hemapoietic cells and their subsequent transplantation is the dog. Harvested autologous bone marrow may be established in a long-term marrow culture system (LTMC) (Carter et al., Exper. Hematol. 18:995–1001, 1990). Following infection with a retroviral stock, the marrow may be cultivated, and adherent cells may be recovered for infusion into the autologous recipient. A fraction of the transduced cells may be retained for determining transduction efficiency by calculating the ratio of colonies that grow in the presence or absence of a selection agent, such as G418.

The vectors of the invention may be transduced into human bone marrow cells. Human bone marrow may be recovered and fractionated by density gradient centrifugation. The mononuclear fraction may be recovered and exposed to a vector according to the invention under conditions suitable for infection to occur; for example, the harvested bone marrow may be exposed to an effective concentration of transducing vector in a supernatant. The multiplicity of infection, in nonlimiting embodiments, is between 5 and 25 transducing viruses per bone marrow cell. Hemopoietic growth factors may be added to the medium, including stem cell factor, interleukin-6, interleukin-3, and interleukin-1, and GM-CSF. Non-adherent cells may then be transferred to methylcellulose-tissue culture medium, in the presence or absence of the appropriate selection agent. Erythropoietin as well as other growth factors may be used to facilitate growth. Colonies may be ascertained microscopically, and the relative proportions of erythroid (BFU-E and CFU-E), myeloid (CFU-GM) and multipotential (CFU-GEMM) colonies may be determined in the presence and absence of a selection agent. The erythroid cells may be recovered. Expression of the erythroid gene may be determined in pooled colonies by analysis of its mRNA by quantitative S1 protection assay using a erythroid protein-specific probe.

Alternatively, prior to transduction, the proportion of human progenitor and stem cells may be enriched by antigen-CD34+ selection by fluorescence-activated cell sorting or by a column that retains this fraction of cells (e.g., a Cell Pro column). With an initial quantity of preferably greater than $10^9$ human bone marrow cells, a sufficient stem and progenitor cell population may be concentrated for transduction with a smaller volume of viral stock. For progenitor cell-enriched marrow, a multiplicity of infection of between $5\times10^3$ and $25\times10^3$ virus particles per cell may be preferably used.

Where the vector integrates into the host chromosome, analysis of the integration efficiency and stability in transduced bone marrow cells may be performed by Southern blotting of genomic DNA. Determination of the level of erythroid protein expression in the transduced cells may be performed by standard techniques for RNA and protein analysis.

In an alternate embodiment of the invention, long-term bone marrow cultures (LTMC) may be established (Bienzle et al., Proc. Natl. Acad. Sci. 91:350–354, 1994; Fraser et al., Blood 76:1071–1076, 1990; Nolta et al., Blood 75:787–797, 1990; Carter et al., Blood 79:356–364, 1992). Cells may be transduced as described above and analyzed similarly.

5.5. Transplantation of Transduced Bone Marrow Cells

The transduced bone marrow cells described in Section 5.4, supra, may be transplanted into a suitable host and thereby used to produce erythroid cells carrying the erythroid gene introduced by transduction.

For example, transduced murine bone marrow cells may be injected into mice which have been lethally irradiated to achieve bone marrow ablation. Mice may be maintained for various periods post-transplantation to assess the persistence of erythroid protein expression from the transduced gene. In addition, bone marrow, thymus and spleen samples may be recovered post-sacrifice to determine the extent to which these tissues have been populated with cells containing the transduced gene. For example, host mice may be sacrificed and spleen colony-forming units (CFU-S) may be recovered after about 10–12 days for DNA and RNA analysis. Where appropriate, Southern blotting of the DNA with a suitable probe will determine if the vector has integrated. S1 analysis of the RNA can be performed to ascertain the level of erythroid gene expression. Further, after a significant period post-transplantation, for example, 6 months, bone marrow may be recovered from the recipient mice for secondary transplantation into lethally irradiated mice to determine the efficiency of transduction of the true hematopoietic stem cells. The repopulating capacity of the transduced bone marrow can be assessed by DNA and RNA analysis as described above.

Where the dog animal model system is used, the transduced canine bone marrow described in Section 5.4, supra, may be infused into a recipient. Use of the LTMC-derived cells does not require bone marrow ablation (Bienzle et al., Proc. Natl. Acad. Sci. 91:350–354, 1994) due to competitive repopulation of the bone marrow by the transduced cells.

Transduced human bone marrow cells may be transplanted into a human host using standard techniques for autologous or allogeneic bone marrow transplant (see, for example, Armitage, N. Engl. J. Med. 330:827–838, 1994).

5.6. Gene Therapy in Animal Models of Human Globin Diseases

The ability of vectors of the invention to treat human globin diseases may be evaluated using animal models of such disorders.

For example, transgenic mouse models of sickle cell anemia have been developed by introducing a human β-globin gene carrying sickle and other mutations conferring decreased oxygen affinity and increased polymerization of the hemoglobin molecule (Trudel et al., EMBO J. 10:3157–3165, 1991). Such mice may be used to evaluate the ability of a vector of the invention, for example, N2A-γ, to reverse the sickle cell phenotype. DNA and RNA analyses may be used to assess the integration of the viral sequences carrying the γ-globin gene (where appropriate) as well as the level of globin expression. The anemia of the animals may be monitored as well as the pathology of the red blood cells to determine if the sickling of the cells is decreased. These assessments may be performed under conditions of ambient as well as low oxygen tension.

As a second example, a mouse model for β-thalassemia results from the deletion of a 3.3 kb region of the $B^{maj}$ gene in DBA/2J mice (Skow et al., Cell 34:1043–1052, 1983) (available from the Jackson Laboratory, Bar Harbor, Me.). These mice may be used to study the ability of a vector according to the invention, for example, N2A-γ, to transduce autologous bone marrow that is transplanted back into the mice. The introduction of the fetal γ-globin gene into these animals may be beneficial in view of human individuals homozygous for hereditary persistence of fetal hemoglobin (HPFH) who compensate for the deletion of both β-globin genes with increased production of fetal γ-globin and who are asymptomatic (Bunn, H. F. and Forget, B. G. *Hemoglobin: Molecular, genetic and clinical aspects* (Saunders, Philadelphia, 1986). Transplantation of transduced bone marrow may be performed as previously described in Section 5.5, supra. The mice may be subjected to bone marrow ablation if needed; chimerism of bone marrow, if ablation is not performed, however, may still ameliorate the manifestations of the disease (van den Bos et al., BMT 12:9–13, 1993). DNA and RNA analyses may be used to assess the integration of the viral sequences carrying the γ-globin gene as well as the level of globin expression. The hematology of these animals can be monitored for several parameters, including CBC count, reticulocyte number, and inclusion bodies to assess restoration of normal hematologic status.

5.7. Utilities of the Invention

The vectors of the invention have a number of in vivo and in vitro utilities.

In a first series of embodiments, the invention may be used to introduce a normal erythroid gene into cells which exhibit a deficiency or defect in the protein encoded by the erythroid gene. In this regard, in specific, nonlimiting embodiments of the invention, a vector of the present invention may be used to introduce a normal globin gene into erythroid cells derived from patients with sickle cell anemia or β-thalassemia. For example, and not by way of limitation, vectors of the invention may be used to restore normal β-globin function to cells derived from sickle cell anemia and β-thalassemia patients. Transduction of bone marrow (preferably autologous) from individuals afflicted with these diseases with vectors of the invention followed by retransplantation is a promising modality for permanent correction of the genetic defect in these disorders. Accordingly, the present invention provides for a method of treating a subject suffering from sickle cell anemia comprising administering, to a subject in need of such treatment, an effective concentration of a vector of the invention (e.g. a vector comprising the human fetal γ-globin gene). Such vector may be administered by exposing bone marrow cells of the subject to an infectious concentration of the vector. β-globin diseases may be treated by gene therapy using retroviral vectors containing the β-globin, fetal γ-globin, epsilon-globin, $^A$γ-globin or $^G$γ-globin genes. In the case of sickle cell anemia, it may be preferable to comprise a gene encoding human fetal γ-globin into vectors of the invention.

A similar approach may be used in treating the α-thalassemias by engineering an α-globin gene into the vector. The α-globin diseases can be treated with retroviral vectors containing the zeta-globin or α-globin genes. Accordingly, the present invention provides for a method of treating a subject suffering from β-thalassemia comprising administering, to a subject in need of such treatment, an effective concentration of a vector of the invention (e.g. a vector comprising the human fetal γ-globin gene or the β-globin gene). Such vector may be administered by exposing bone marrow cells of the subject to an infectious concentration of the vector and introducing the marrow cells, containing the vector, into the subject.

Other non-globin-based diseases of the red blood cell are amenable to treatment with the methods and vectors of the present invention. The αLCR may activate the expression of any gene in an erythroid cellular environment. Application of the methods described, supra, to such diseases as sex-linked sideroblastic anemia (a defect in delta amino levulonic acid synthase), porphyrias (such as, but not limited to, erythropoietic porphyria resulting from a defect in ferrochelatase, congenital erythropoietic porphyria resulting from a defect in uroporphriniogen III cosynthetase), hemolytic anemia associated with glucose-6 phosphate-dehydrogenase deficiency, congenital spherocytic anemia resulting from a defect in spectrin, congenital elliptocytosis resulting from a defect in protein 4.1, and other erythroid disorders are within the scope of the invention. In an example where transduction of a large gene is required to treat a specific condition, use of a "minigene" or cDNA cloned into a suitable vector may circumvent size limitations.

Vectors of the invention may have broader application in the delivery of non-globin genes to erythroid cells. For example, the red blood cell may be engineered to express a heterologous gene under the control of the αLCR in order to serve as a reservoir for a needed protein. These proteins include such biologically necessary molecules as hormones, growth factors, and include, but are not limited to, insulin, growth hormone, thyroxin, G-CSF, GM-CSF, interleukins, EPO, as well as many other proteins.

In a second series of embodiments, the vectors of the present invention may be used to transfer an erythroid gene into stem cells that acts as a marker and allows lineage tracing as these transplanted stem cells populate and circulate in a recipient. The gene may be detected by Southern blotting of genomic DNA to score for the integrated sequence (Fraser et al., Blood 76:1071–76, 1990).

In a third series of embodiments, a globin gene may be "marked" by the alteration of several nucleotides so as to distinguish it from the wild-type sequence and to determine expression levels of a transduced globin relative to endogenous globin by techniques such as RNase protection analysis of mRNA or protein detection techniques.

In a fourth series of embodiments, the vectors of the invention may be used to produce animal models for human erythroid diseases. For example, a vector comprising a human sickle β-globin gene and a normal human α-globin gene may be used to create a transgenic animal which may be used as a model system for sickle cell anemia.

In a fifth series of embodiments, vectors comprising an erythroid gene, e.g., a globin gene, may also be used as a control construct in co-transfection applications, in which the efficiency of transfection of a second vector may be ascertained by determining globin expression. This is feasible because globin detection is well known to those skilled in the art, whether by means of mRNA detection as in an S1 analysis using globin probes, or by detection of the globin protein using a Western Blot or immunohistochemistry with anti-globin antibodies.

In a sixth series of embodiments, the vectors of the present invention may be used to identify a minimal αLCR sequence that is capable of directing expression of a heterologous gene, for example, a globin gene.

6. EXAMPLE: CLONING OF N2A-γ VECTOR

The N2A vector contains a neomycin resistance (neo$^r$) gene flanked by the 2 long terminal repeats (LTRs) from Moloney murine leukemia virus (Armentano, et al., J. Virol. 61:1647–1650, 1987; Hantzopoulos, et al., Proc. Natl. Acad. Sci. 86:3519–3523, 1989). The human γ-globin gene was cloned at the unique XhoI site between the neo$^r$ gene and 3' LTR in a reverse transcriptional orientation relative to the 5' LTR as a 2.2 kb RsaI fragment (−410 to +1761 of the gene sequence) (SEQ ID NO.5.).

The αLCR fragment was generated by the polymerase chain reaction by amplifying 0.5 μg of human DNA using primers designed from the 356 bp fragment (SEQ ID NO:7) (the sequence of which is set forth in FIG. 7) shown by Jarman et al., Mol. Cell. Biol. 11:4679–4689, 1991, to account for the major activity of the αLCR. The sequence of primer 1 was 5'TCTGGAACCTATCAGGGAC-3' (SEQ ID NO:1) and that of primer 2 was 5'-CTCTCAGATAAACAGGAGGGGG-3' (SEQ ID NO:2). Amplification parameters included 30 cycles of synthesis, each consisting of denaturation for 1 minute at 94° C., annealing for 2 minutes at 45° C., and extension for 3 minutes at 72° C. The resulting 255 bp product (SEQ ID NO:6), having a sequence as set forth in FIG. 6, was eluted from a preparative agarose gel, blunt-ended by DNA polymerase, and cloned into the SmaI cloning site of pBluescript II KS (Strategene, La Jolla, Calif.) for plasmid preparation by standard techniques to generate a fragment stock. The fragment was cloned into the BglII site of the polylinker in the 3' LTR by blunt-end ligation, to produce the plasmid designated N2A-γ.

7. PRODUCTION OF N2A-γ VECTOR FROM PRODUCER CELL LINES

Three retroviral packaging cell lines, GP+envAM12 (Markowitz, D. et al., Virology 167:400–406, 1988), GP+E-86 (Markowitz, D. et al., J. Virol. 62:1120–1124, 1988), and PA 317 (ATCC accession no. CRL-9078; Miller, A. D. et al., Mol. Cell Biol.6:2895–2902, 1986) were transfected with 20 micrograms of N2A-γ by electroporation. After 24 hours, the cells were split 1:5 and G418 was added to a final concentration of 400 μg/ml. Colonies that formed after 2 weeks were isolated using cloning cylinders and expanded to create into producer cell lines.

The efficiencies of the producer cell lines were analyzed by determining retroviral titers. The viruses were precipitated from the supernatant of the cell line by adding 0.5 volume of polyethylene glycol (30% PEG, 1.5 M NaCl). This was followed by the addition of lysis buffer (0.1% SDS, 0.3M NaCl, 10 mM EDTA, 10 mM Tris pH 7.4), followed by phenol/chloroform extraction. Nucleic acid was precipitated in 70% ethanol and resuspended in water. The nucleic acid was denatured in formaldehyde and applied to a slot-blot apparatus. A radiolabeled probe containing $neo^r$ sequences was used to hybridize to the immobilized RNA. Quantitation was performed by densitometric scanning. Viral stocks of known titer were also slot-blotted and probed to act as a standard in a signal:titer determination.

The titers of the stocks are given in TABLE 1. High titer stocks produced from GP+envAMV ($7\times10^6$) were used in the transduction experiments.

TABLE 1

TITERS OF RETROVIRAL STOCKS

| Packaging Cells | Host Range | Titers > $1 \times 10^6$ | Highest Titer |
|---|---|---|---|
| GP + envAMV | Amphotropic | 3/9 | $7 \times 10^6$ |
| PA317 | Amphotropic | 0/10 | $1 \times 10^5$ |
| GP + E86 | Ecotropic | 3/9 | $5 \times 10^6$ |

8. EXAMPLE: ANALYSIS OF RETROVIRAL INTEGRATION IN PRODUCER CELL LINES

Genomic DNA from the producer cell lines was isolated, digested with SalI and electrophoresed on a 1% agarose gel. The DNA was transferred to a nylon membrane and hybridized to a radiolabeled probe corresponding to the αLCR sequence. The expected size of an unrearranged SalI fragment was 4.3 kb.

FIG. 2 shows an autoradiograph of the Southern blot for the producer cell lines; 9 of the 12 lines contained the intact 4.3 kb fragment, indicating that stable integration had occurred. A summary of the Southern blot analysis from all colonies isolated from the 3 packaging cell lines is presented in TABLE 2.

TABLE II

IN VITRO TRANSDUCTION OF MURINE BONE MARROW PROGENTIORS

| Experiment Number | Retroviral Construct | Colonies Analyzed | Colonies Transduced | Efficiency of Transduction |
|---|---|---|---|---|
| 1 | N2 | 20 | 3 | 15% |
| 1 | N2A-γ | 20 | 6 | 30% |
| 2 | N2 | 20 | 5 | 25% |
| 2 | N2A-γ | 20 | 4 | 30% |
| 1 + 2 | N2 | 40 | 8 | 20% |
| 1 + 2 | N2A-γ | 40 | 10 | 25% |

9. EXAMPLE: INFECTION OF NIH 3T3 CELLS

Adherent NIH 3T3 cells were infected with the N2A-γ vector in the presence of 4 μg/ml polybrene. G418 was added to a final concentration of 400 μg/ml. Cell colonies that were resistant to G418 were expanded. 10 μg of genomic DNA was digested with XbaI and analyzed by Southern blotting with an αLCR probe as described in Section 8, supra. The presence of a 3 kb XbaI fragment indicated stable integration of the retrovirus in addition to a variable fragment that results from junctional sequences at the site of chromosomal integration.

Results of the Southern blot for the NIH 3T3 colonies are shown in FIG. 3, where 6 of 8 colonies exhibited intact retroviral integration.

10. EXAMPLE: EXPRESSION OF THE γ-GLOBIN GENE BY INFECTION OF MOUSE ERYTHROLEUKEMIA CELLS WITH N2A-γ

Mouse erythroleukemia (MEL) cells were infected with N2A-γ by co-cultivation with producer cell lines as described in Plavek et al., Blood 81:1384–1392, 1993. G418 was added to the medium to a final concentration of 400 μg/ml to select for $neo^r$ colonies. 8 colonies were analyzed by Southern blot, as described in Section 8, supra, to confirm that retroviral integration had occurred.

The colonies were expanded then induced with 1.2% DMSO for 72 hours. Cytoplasmic RNA was isolated and analyzed for $B^{maj}$ and human γ-globin expression by S1 analysis.

A 5' end-labelled probe that detects human γ-globin mRNA and a 3' end-labelled probe that detects mouse $B^{maj}$ mRNA were mixed and used together to measure mouse and human globin mRNA simultaneously in the same S1 experiment.

Figure 4A:
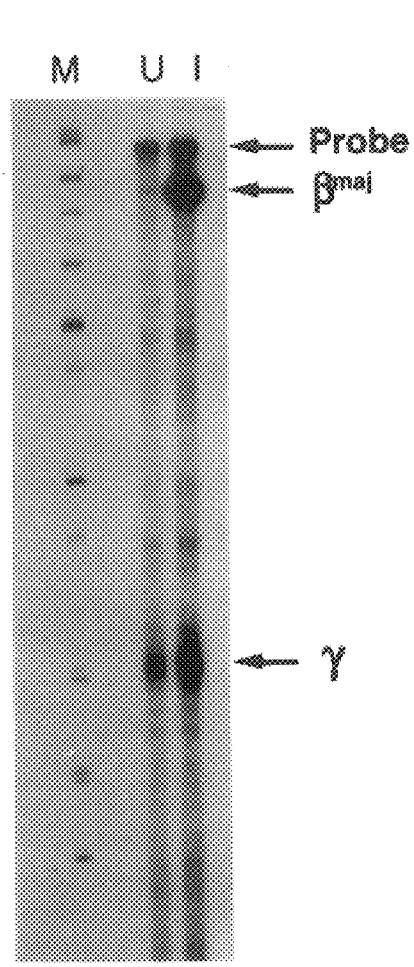

FIG. 4A shows the results of the analysis of globin mRNA expression in infected MEL cells. DMSO induction was verified by the marked increase in mouse $B^{maj}$ mRNA in induced cells as compared to uninduced cells. The transduced human γ-globin gene was also expressed at a high level upon induction. After correction for differences in the specific activities of the mouse and human probes, the level of expression of the human γ-globin gene was found to be equivalent to that of a single mouse $B^{maj}$ globin gene in transduced MEL cells.

Figure 4B:
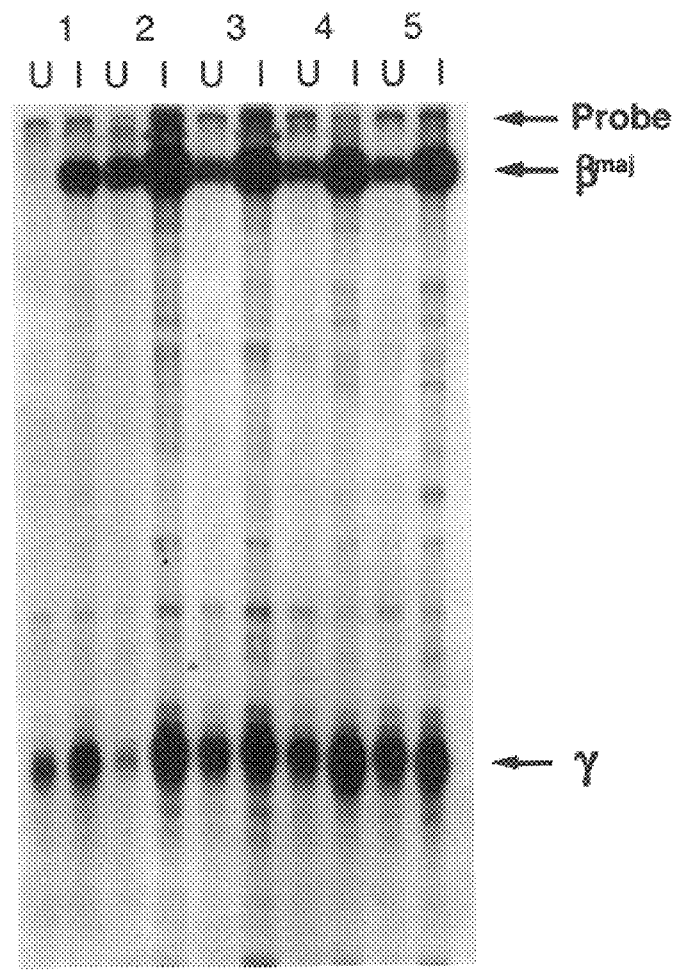

FIG. 4B shows the results from the analysis of 5 unique clones of transduced MEL cells. High inducible expression of the human γ-globin gene is seen in all 5 clones analyzed.

11. EXAMPLE: IN VITRO TRANSDUCTION OF PRIMARY MURINE HEMOPOIETIC PROGENITORS

Murine bone marrow cells were obtained from femurs of adult BALB/c mice. 5×105 bone marrow cells were resuspended in 1 ml of retroviral stocks (amphotropic N2A-γ: 7×10⁶ cfu/ml; ecotropic N2: 1×10⁷ cfu/ml) supplemented with 5 μg/ml polybrene and incubated overnight at 37° C. in a humidified 5% $CO_2$ incubator. The bone marrow cells were washed the next day and plated in 0.8% methylcellulose supplemented with 1% bovine serum albumin, 10% fetal calf serum, 0.1 mM 2-mercaptoethanol, 2 mM L-glutamine, 2% spleen cell conditioned medium and 1 U/ml recombinant murine erythropoietin at a final cell concentration of 3×10⁴ cells/ml. Colonies that formed were isolated between days 10–12 and lysed in 0.4 ml of DNA extraction buffer. One third of the DNA isolated from each colony was used in a polymerase chain reaction (PCR) with primers designed to amplify the neo$^r$ sequences. The PCR amplification reactions were performed in a buffer consisting of 500 mM KCl, 100 mM Tris pH 9, 1% Triton X-100, 25 mM $MgCl_2$, 10 mM of each dNTP, 250 mM of primer 1 and 2, and 1 unit of Taq polymerase. The parameters of the 35 cycles of amplification were as follows: 1 minute of denaturation at 94° C., 1 minute of annealing at 52.5° C. and 2 minutes of extension at 72° C. The sequence of primer 3 was TTTCTGGATTCATCGACTGTGG (SEQ ID NO:3) and the sequence of primer 4 was AAAGTCCT-TGGGGTCTTCTAC (SEQ ID NO.4). The PCR products were electrophoretically separated on a 1% agarose gel and the amplified 842 bp fragments were visualized by Southern blotting using a neo$^r$ probe.

TABLE 2 summarizes the results from the transduction by N2A-γ and N2 retroviruses in two separate experiments. The results of these experiments show that the N2A-γ retrovirus can transduce bone marrow progenitors at least as efficiently as its parental N2 retrovirus.

12. EXAMPLE:IN VIVO ANALYSIS OF TRANSDUCED MURINE BONE MARROW PROGENITORS

1×10⁶ bone marrow cells were resuspended in 2 ml of retroviral stocks (amphotropic N2A-γ:7×10⁶ cfu/ml; amphotropic N2: 1×10⁶ cfu/ml) supplemented with polybrene to a final concentration of 5 μg/ml. After overnight incubation at 37° C., the bone marrow cells were washed and resuspended in RPMI 1640 medium supplemented with 2% fetal calf serum at a final cell concentration of 10⁵ cells/ml. 5× 10⁴ cells were injected into the tail vein of lethally irradiated (900 rad) BALB/c mice. After 12 days, the mice were sacrificed by cervical dislocation and spleen colony-forming units (CFU-S) were dissected from the spleen and lysed in 0.4 ml of DNA extraction buffer. DNA isolation, PCR amplifications and Southern blotting were performed as described supra.

27 CFU-S colonies were isolated from 4 mice reconstituted with bone marrow infected with the N2 retrovirus. 19 of these 27 colonies showed integration of neor sequences by PCR analysis. 17 CFU-S colonies were isolated from 4 mice reconstituted with N2A-γ virus-infected bone marrow cells. 13 of these 17 colonies were positive for neo$^r$ sequences and αLCR sequences by PCR analysis. These experiments demonstrate that the efficiency of CFU-S transduction by the N2A-γ retroviruses (76%) is at least as high as the efficiency of transduction by the N2 retroviruses (70%).

N2A-γ was deposited with the American Type Culture Collection, 10801 University Boulevard, Manasses, Va. 20110, on Mar. 2, 1995 and assigned accession no. 97077.

Various publications are cited herein, the contents of which are hereby incorporated by reference in their entireties.

I claim:

1. A vector comprising a gene from the β-globin gene cluster operably linked to a human α-globin locus control region.

2. The vector of claim 1 wherein the vector is a retroviral vector.

3. The vector of claim 1 wherein the gene is selected from the group consisting of β-globin epsilon-globin, $^A$γ-globin, and $^G$γ-globin.

4. The vector of claim 1 wherein the gene is a human fetal γ-globin gene.

5. The vector of claim 2 wherein the gene is a human fetal γ-globin gene.

6. The vector of claim 5 which is N2A-γ, as deposited with the American Type Culture Collection and assigned accession number 97077.

7. An erythoid cell, isolated from an individual, containing a gene from the β-globin gene cluster operably linked to a human α-globin locus control region.

8. The cell of claim 7 wherein the gene is selected from the group consisting of β-globin, epsilon-globin, $^A$γ-globin, and $^G$γ-globin.

9. The cell of claim 8, wherein the gene is a human fetal γ-globin gene.

10. A producer cell containing a retroviral vector comprising a gene from the β-globin gene cluster operably linked to a human α-globin locus control region.

11. The producer cell of claim 10 wherein the gene is selected from the group consisting of β-globin, epsilon-globin, $^A$γ-globin, and $^G$γ-globin.

12. The producer cell of claim 10 wherein the gene is a human fetal γ-globin gene.

* * * * *